Feb. 18, 1941. M. FASCELL Plant Pat. 451
MANGO
Filed Sept. 23, 1940
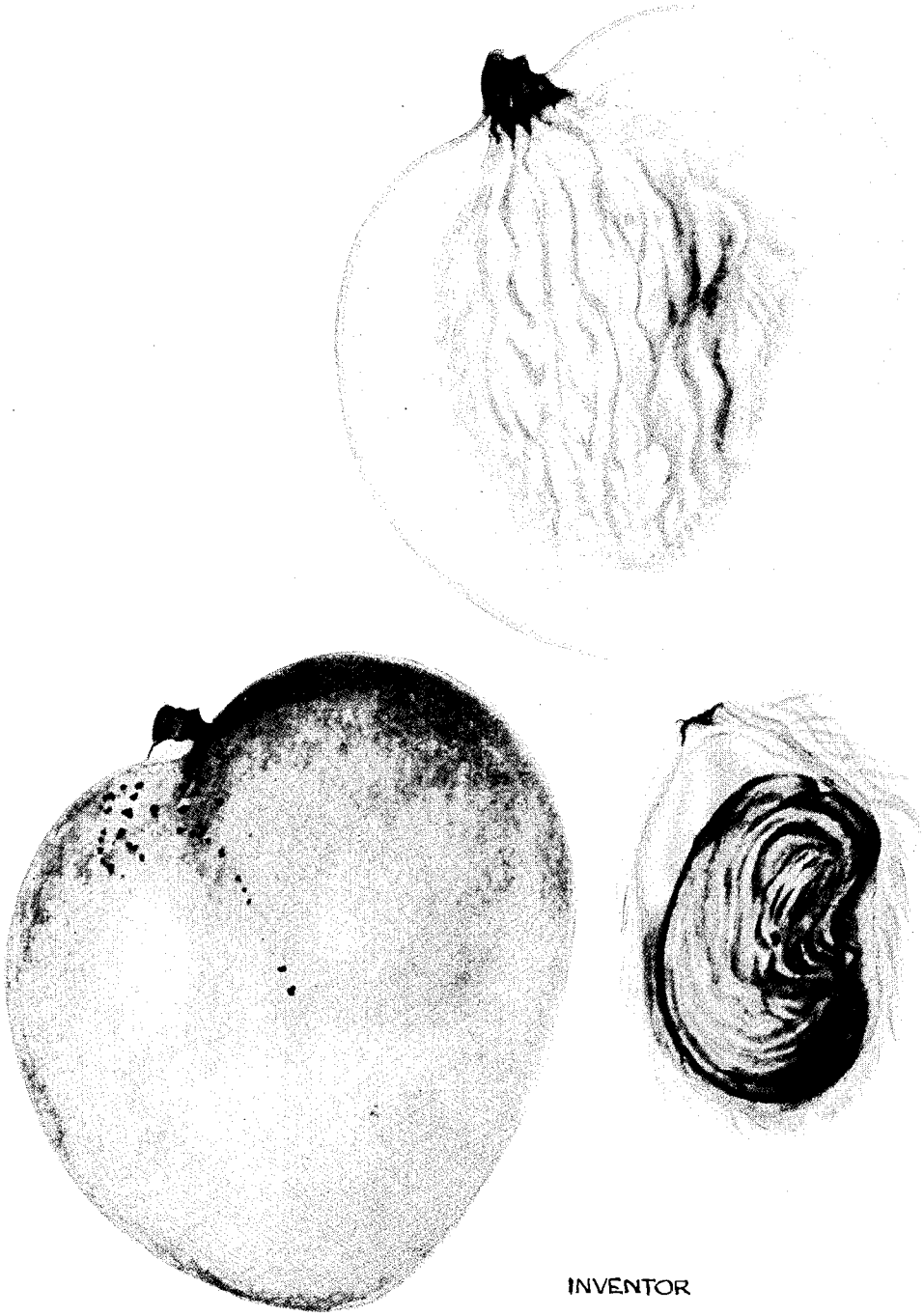
INVENTOR
Michael Fascell
By Orville M Kile
PLANT PATENT AGENT Patented Feb. 18, 1941

Plant Pat. 451

UNITED STATES PATENT OFFICE

451

MANGO

Michael Fascell, Miami, Fla.

Application September 23, 1940, Serial No. 358,015

1 Claim. (Cl. 47—62)

My invention relates to a new and distinct variety of mangoes which is the result of definite cross-pollination carried on by me. My principal aim was to produce a variety of mango which would extend the mango season with a good quality mango which would also bear a heavy crop. I therefore crossed the Haden with the Brooks Late. The former is an early variety of excellent quality but bears a very light crop. The latter is a late variety of rather poor quality but bearing a very heavy crop.

From this cross there resulted three seedlings, one of which fruited in its fourth year, the fruit proving to be superior in many respects to that of either of its parents, although more like the Haden than any other known variety.

The new variety combines the best qualities of its parents, its growth being much like Brooks Late and its fruit being much like Haden, with its maturing season beginning shortly after Haden and extending for a full four weeks thus filling the gap between Haden and Brooks Late. My aims as to extension of the season were accomplished and in addition a fruit of much superior eating qualities was produced.

The fruit of this new variety is very highly colored and attractive in appearance as well as very firm-fleshed and of excellent flavor. Its keeping and shipping qualities are above the average. This latter quality is probably the result of the longer period required for ripening.

The original illustrations accompanying this application show in approximately true colors; a full side view of the fruit of my new variety taken from one of the flattened sides, a cross-section view showing the flesh, and an outline drawing showing the unusual shape of the inner seed.

Following is a detailed description of this new variety of mango. Colors are indicated by reference to Ridgway's Color Standards and Nomenclature except where obviously the ordinary dictionary term is intended.

*The tree*

Growth: Vigorous and spreading, in contrast with the symmetrical and dense growth of the Haden. This spreading growth allows the sun to penetrate through the foliage so that the fruits in the center of the tree are almost as colorful as those on the outer edge.

New wood: Vigorous and of reddish purple color.

Bearing: Very prolific.

Foliage: Abundant but not dense, due to spreading growth of tree.

*Leaves.*—*Size*—medium. Seven to nine inches long, 1¾ to 2½ inches wide at their broadest point. *Shape*—long and narrow, with acute apex. *Margin*—entire. *Veins*—twenty to 25 pairs of transverse veins. *Position*—upright in growth but with tendency to bend downward when fully matured. *Color*—popularly called fern green. The nearest in Ridgway's is Cedar Green (Plate VI) but the leaves are glossy and much brighter. Veins and heavy midrib are Cosse Green (Plate V). The under side of the leaf is Cosse Green except for the midrib which has a yellowish tinge. *Aspect*—waxy and glossy. Undulating. *Texture* — exceptionally heavy. *Leaf stem*—very short.

*The flower*

The flowers appear in very large panicles much like those of the Haden. As they come into full bloom, they get top-heavy and bend downwards.

Panicles:

*Size.*—Usually very large, measuring 12 to 18 inches in length.

*Shape.*—Long; slender; dropping when in full bloom.

*Flowering season.*—Same as Haden.

*Blossoms.*—Large; abundant; high percentage botanically "perfect"; noticeably redder than blossoms of the Haden variety.

*The fruit*

Maturity:

*Season.*—Mid-season variety, usually matures from June 15 to August 15. Ripens soon after Haden crop is over and before Brooks Late begins. Full four weeks maturing season.

*Habit.*—Although this variety comes into bloom at the same time as the Haden, the fruit ripens fully four weeks later. A check in the 1939–40 season showed requirement of 122 days from the time the fruit had set until it ripened, in the case of the Haden. Under the same conditions, the new variety required 152 days to ripen.

Perishability: The long-ripening range produces a fruit of better keeping quality than other known varieties and it is therefore an unusually good shipper. A tree-ripened Haden fruit kept at room temperature becomes too ripe to eat after five days, but the fruit of my new variety, kept under the same conditions, is found to be firm and in good eating condition after about eight days.

Color: The color of the fruit is very bright and attractive. When fully ripe the upper portion resembles the Haden but with brighter cheeks upon which the red color is more uniform and extends farther downward. This blush includes various shades of red, the most outstanding being between Eugenia Red and Light Jasper Red (Plate XIII). The lower portion is blushed with Apricot Yellow (Plate IV). Many tiny yellow dots are distributed over the surface, but these are much less conspicuous than those on the Haden fruit.

Size: Above the average; about 4 inches long by 3½ inches wide. Weight 12 to 20 ounces.

Flesh: When fully ripe the flesh holds firm around the seed, not mushy as is often found to be the case in other varieties of this general class.

*Texture.*—Very fine, firm and juicy.

*Color.*—Orange.

*Flavor.*—Mellow and rich; sub-acid to sweet; somewhat similar to the flavor of pineapple.

*Aroma.*—Pleasantly fragrant when fruit is ripe.

Form: Plump; oval to ovate; base rounded; apex broadly pointed; somewhat unsymmetrical when viewed from the flattened side, but when viewed from the narrower side, the halves are nearly equal and symmetrical. It is more flattened in shape than the fruit of the Haden. Practically no indentation occurs on the lower portion of the fruit.

Skin: Smooth and thin, yet tough and resistant. Usually has very few black spots.

Fiber: Has less fiber than is found in the fruit of most varieties.

Seed:

*Shape.*—Shell of seed is similar in shape to that of Haden, but the seed inside the shell is entirely different, whereby it can easily be distinguished. There is a much sharper point on one side of the seed of my new variety and little indentation on the lower portion.

*Attachment.*—When the fully ripened fruit is cut longitudinally and the seed given a few gentle twists, it can be pried out and the fruit eaten from the halved sections, much like cantaloupe. This is possible because the seed is nearly free rather than the usual cling.

*Comparisons*

My new variety is more like the Haden variety than any other known to me. The following are the most important points which distinguish my variety from Haden and other varieties.

1. The ripening season of its fruit falls between that of Haden and Brooks Late.

2. My variety has a much longer range of maturity from blossoming date to ripening date, than Haden or other known varieties.

3. My variety has a ripening season of four full weeks or more and this is considerably longer than that of Haden and other known varieties.

4. The growth of the tree is more spreading than that of Haden.

5. The panicles are much larger than most varieties.

6. The flowers are noticeably redder than those of Haden, slightly larger, and a greater percentage botanically perfect.

7. Its fruit has superior shipping and keeping qualities as compared with Haden.

8. The fruit is a brighter color than Haden or other known varieties.

9. The flavor of the fruit is unique for mangoes, being considerably more like the flavor of the pineapple.

10. The flesh of the fruit is firmer than that of Haden, particularly around the seed.

11. The skin of the fruit is smoother and thinner than that of Haden, although as tough.

12. The fruit is not so plump in shape as Haden but has a somewhat flattened appearance.

13. The yellow dots on the skin are much smaller and much less prominent than on Haden.

14. The fruit has no noticeable depression or bump on the lower portion such as is found on the fruit of Haden.

15. The seed is practically free and has much less fiber than Haden and many other varieties.

16. The inner seed has a very sharp point on one side, while the seed of Haden is much less pointed.

17. The tree is a much more prolific bearer than the Haden, bearing somewhat like the Brooks Late.

Having thus disclosed my invention, I claim:

The new and distinct variety of mango herein described with its fruit herein illustrated, characterized particularly by the spreading, vigorous growth of the tree; the long and continuous intermediate maturing season; the unusually long range between blossoming and fruit maturity; the prolific production of its fruits throughout the long season; its medium-sized, slightly flattened ovate fruits with firm orange-colored flesh, pleasant aroma, unique pineapple-like flavor, thin tough smooth skin of bright red to apricot yellow, and relatively greater freedom from fiber; the distinctive shape of the inner seed of its fruit; and the ability of its fruit to keep unusually long after ripening.

MICHAEL FASCELL.